United States Patent [19]
Hirokawa et al.

[11] Patent Number: 6,074,859
[45] Date of Patent: Jun. 13, 2000

[54] MUTANT-TYPE BIOLUMINESCENT PROTEIN, AND PROCESS FOR PRODUCING THE MUTANT-TYPE BIOLUMINESCENT PROTEIN

[75] Inventors: Kozo Hirokawa; Naoki Kajiyama; Seiji Murakami, all of Chiba, Japan

[73] Assignee: Kikkoman Corporation, Noda, Japan

[21] Appl. No.: 09/111,752

[22] Filed: Jul. 8, 1998

Related U.S. Application Data

[60] Provisional application No. 60/051,917, Jul. 8, 1997.

[51] Int. Cl.⁷ ........................................ C12N 9/02
[52] U.S. Cl. .......................... 435/189; 435/440; 435/441; 435/69.1; 435/71.1; 435/71.2; 435/8; 530/858
[58] Field of Search ............................... 435/8, 69.1, 71.1, 435/71.2, 440, 441, 189; 530/858

[56] References Cited

U.S. PATENT DOCUMENTS

| | | | |
|---|---|---|---|
| 5,229,285 | 7/1993 | Kajiyama et al. | 435/189 |
| 5,843,746 | 12/1998 | Tatsumi et al. | 435/189 |

OTHER PUBLICATIONS

Kajiyama et al., Isolation and Characterization of Mutants of Firefly Luciferase Which Produce Different Colors of Light, Protein Engineering, 4 (6):691–693, 1991.

Wood et al., Bioluminescent Click Beetles Revisited, J. Biolumin. Chemilum. 4: 31–39, Jul. 1989.

De Wet et al., Cloning of Firefly Luciferase cDNA and the Expression of Active Luciferase in *Escherichia coli*, PNAS 82: 7870–7873, Dec. 1985.

Masuda et al. Cloning and Sequence Analysis of cDNA for Luciferase of a Japanese Firefly, *Lucioloa cruciatea*, Gene 77: 265–270, 1989.

Kajuyama et al., Purification and Characterization of Luciferases from Fireflies, *Luciola Cruciata* and *Luciola lateralis*, Biochim. Biophys. Acta. 1120:228–232, 1992.

*Primary Examiner*—Rebecca E. Prouty
*Assistant Examiner*—Richard Hutson
*Attorney, Agent, or Firm*—Oblon, Spivak, McClelland, Maier & Neustadt, P.C.

[57] ABSTRACT

According to the present invention, there can be provided a bioluminescent protein, luciferase excellent in thermostability etc. and with high catalytic efficiency.

12 Claims, 1 Drawing Sheet

MUTANT-TYPE BIOLUMINESCENT PROTEIN, AND PROCESS FOR PRODUCING THE MUTANT-TYPE BIOLUMINESCENT PROTEIN

This application claims benefit of priority under 35 U.S.C. § 119(e) to U.S. Provisional Application Serial No. 60/051,917, filed on Jul. 8, 1997.

FIELD OF THE INVENTION

The present invention relates to a mutant-type bioluminescent protein and a process for producing the mutant-type bioluminescent protein.

BACKGROUND OF THE INVENTION

As conventional wild-type firefly luciferases, those derived from Genji firefly (*Luciola cruciata*), Heike firefly (*Luciola lateralis*), North American firefly (*Photinus pyralis*), East European firefly (*Luciola mingrelica*), Tuchi firefly (*Lampyris noctiluca*) etc. are known.

Further, mutant-type luciferases (with mutations in thermostability, luminescent color etc.) have also been obtained from these wild-type firefly luciferases as the source.

Improvement of the catalytic efficiency and stability of this enzyme by mutating it is very important. This is because the improvement of catalytic efficiency leads to a reduction in the enzyme used while the improvement of stability makes the enzyme usable under reaction conditions which the wild-type enzyme could not be used.

However, none of such luciferases excellent in stability such as thermostability etc. and with high catalytic efficiency have been reported until now.

SUMMARY OF THE INVENTION

Under these circumstances, the present inventors have extensively studied to obtain mutant-type luciferases excellent in stability and with high catalytic efficiency. As a result, the present inventors found that mutant-type luciferases with improvements in catalytic efficiency and/or thermostability are obtained by replacement, alternation, removal and addition of at least one amino acid and fusion of a plurality of luciferases.

That is, the present invention encompasses:

(1) A bioluminescent protein with improvements in catalytic efficiency or stability.
(2) A bioluminescent protein according to (1), wherein the improvements includes at least one of 5 kinds of improvements in substrate specificity and maximum reaction rate in respect of catalytic efficiency, and thermal stability, pH stability and stability at low ion concentration in respect of stability.
(3) A bioluminescent protein according to (1) or (2), which is a luciferase derived from beetles (Coleoptera).
(4) A bioluminescent protein according to (1) or (2), which is a luciferase derived from fireflies.
(5) A process for producing the bioluminescent protein of (1) or (2), which comprises modifications to a bioluminescent protein precursor.
(6) A process for producing the bioluminescent protein of (1) or (2), wherein said modifications involve the replacement, alternation, removal and addition of at least one amino acid and the fusion of a plurality of proteins.
(7) A bioluminescent protein according to (1) or (2), which has firefly luciferase activity and comprises a plurality of firefly luciferases fused therein.
(8) A bioluminescent protein according to (1) or (2), which has firefly luciferase activity and comprises luciferases from Genji firefly (*Luciola cruciata*) and American firefly (*Photinus pyralis*) fused therein.
(9) A bioluminescent protein according to (1) or (2), which has firefly luciferase activity and comprises luciferases from Heike firefly (*Luciola lateralis*) and American firefly (*Photinus pyralis*) fused therein.
(10) A bioluminescent protein according to (1) or (2), which has firefly luciferase activity and comprises luciferases from Genji firefly (*Luciola cruciata*) and Heike firefly (*Luciola lateralis*) fused therein.
(11) A bioluminescent protein according to (1) or (2), which has firefly luciferase activity and has a mutation in an amino acid residue corresponding to the 219-position of the *Luciola cruciata* luciferase.
(12) A bioluminescent protein according to (1) or (2), which has firefly luciferase activity and has a mutation in an amino acid residue corresponding to the 239-position of the *Luciola cruciata* luciferase.
(13) A bioluminescent protein according to (1) or (2), which has firefly luciferase activity and has a mutation in an amino acid residue corresponding to the 290-position of the *Luciola cruciata* luciferase.

DETAILED DESCRIPTION OF THE INVENTION

Hereinafter, the present invention is described in detail.

The "luciferase with improvements in pH stability" as used herein refers to the enzyme having any of the following properties: (1) the one with a broadened pH range in which 80% or more residual activity is maintained, as compared with the conventional luciferase, (2) the one with increased residual activity in a specific pH buffer, as compared with the conventional luciferase, (3) the one with 75% or more residual activity after treatment in 100 mM acetate buffer (pH 5.5) at 25° C. for 22 hours, and (4) the one with 10% or more residual activity after treatment in 100 mM CHES buffer (pH 9.0) at 25° C. for 22 hours.

To provide luciferase with improvements in catalytic efficiency or stability by modifying a gene in the present invention, it is necessary to prepare a wild-type luciferase gene and its recombinant DNA.

The wild-type luciferase gene may be any gene derived from beetles (Coleoptera) and includes e.g. genes derived from Genji firefly (*Luciola cruciata*), Heike firefly (*Luciola lateralis*), North American firefly (*Photinus pyralis*), East European firefly (*Luciola mingrelica*), Tuchi firefly (*Lampyris noctiluca*) etc.

The wild-type luciferase gene derived from *Luciola cruciata* and its recombinant DNA can be obtained by a method as described in e.g. Japanese Patent Laid-Open Publication Nos. 34289/1989 and 51086/1989, and the wild-type luciferase gene derived from *Luciola lateralis* and its recombinant DNA can be obtained by a method described in e.g. Japanese Patent Laid-open Publication Nos. 13379/1990 and 65780/1990.

Then, the resulting wild-type Coleoptera luciferase gene is modified to give a mutant-type luciferase gene. In this modification, the Coleoptera luciferase gene can be modified as such, or the gene is integrated in vector DNA such as plasmid vector, bacteriophage vector etc. and the resulting recombinant DNA may be modified. By these modified luciferase genes, the mutant-type luciferases, in which at least one amino acid in Coleoptera luciferase has been replaced, altered, removed or added and a plurality of Coleoptera luciferases have been fused therein, are prepared.

First, the replacement, alternation, removal and addition of at least one amino acid in the *Coleoptera luciferase* can be effected using a wide variety of methods, for example by contacting the *Coleoptera luciferase* gene or its recombinant DNA with chemicals as mutagen, irradiation with UV light, genetic engineering means or protein engineering means.

The chemicals used as the mutagen in mutagenesis include e.g. hydroxylamine, N-methyl-N'-nitro-N-nitrosoguanidine (NTG), nitrite, sulfite, hydrazine, formic acid, 5-bromouracil etc. The conditions for contacting the chemicals can be varied depending on e.g. the type of chemicals used and are not limited insofar as the desired mutation can be actually induced in the wild-type luciferase gene. Usually, the desired mutation can be induced by contacting the gene with the chemicals preferably at a concentration of 0.5 to 12 M at a reaction temperature of 20 to 80° C. for 10 minutes or more, preferably 10 to 180 minutes. For irradiation with UV light, conventional methods can be followed as described above ("Gendai Kagaku" (Modern Chemistry), pp. 24–30, the June 1989 issue).

As the method of using protein engineering, a means known as site specific mutagenesis can be generally used. Examples are the Kramer method [Kramer, W. et al., Nucl. Acids Res., 12, 9441–9456 (1984); Kramer, W. et al., Methods in Enzymol., 154, 350–367 (1987); Bauer, C. E. et al., Gene, 37, 73–81 (1985)], the Eckstein method [Taylor, J. W. et al., Nucleic Acids Res., 13, 8749–8764 (1985); Taylor, J. W. et al., Nucleic Acids Res. 13, 8765–8785 (1985); Nakamaye, K., et al., Nucleic Acids Res. 14, 9679–9698 (1986)] and the Kunkel method [Kunkel, T. A., Proc. Natl. Acad. Sci., 82, 488–492 (1985); Kunkel, T. A., et al., Methods Enzymol., 154, 367–382 (1987)].

The fusion of a plurality of *Coleoptera luciferases* can be effected by the following methods: a method which comprises introducing desired restriction enzyme site(s) into one or more luciferase genes by site-specific mutagenesis, then cleaving them with a suitable restriction enzyme and linking the resulting fragments from a plurality of luciferase genes; a method which comprises preparing one or more luciferase gene fragments by polymerase chain reaction with specific primers and then linking them; and the DNA shuffling method [Willem P. C. Stemmer, 370, 389–391 (1994)].

In addition to the gene modification methods described above, organic synthesis or enzyme synthesis methods can be used for direct synthesis of the desired modified luciferase gene. The nucleotide sequence of the desired luciferase gene obtained by the above methods can be determined and confirmed using the chemical modification method of Maxam-Gilbert [Maxam and Gilbert, Methods in Enzymol., 6, 499–560 (1980)], the dideoxynucleotide chain termination method using M13 phage [Messing, et al. Gene, 19, 269–276 (1982)] etc. As a matter of course, the desired luciferase can be obtained using a combination of said mutation methods, that is, by a combination of replacement, alternation, removal and addition of at least one amino acid and fusion of a plurality of *Coleoptera luciferases.*

By these mutation means, the mutant-type luciferase gene coding for chimera luciferase, i.e. consisting of a plurality of *Coleoptera luciferases* fused therein, as well as the mutant-type luciferase gene coding for a polypeptide characterized by mutations in amino acid residues corresponding to the 219-, 239- and 290-positions of luciferase from *Luciola cruciata* and *Luciola lateralis,* can be obtained. The mutations in amino acids at the 219-, 239- and 290-positions include e.g. those shown in Table 4.

For instance, the 219-, 239- and 290-positions of luciferase from *Luciola cruciata* and *Luciola lateralis* corresponding to 217-Val, 237-Ile and 288-Val of luciferase from *Photinus pyralis.*

The mutant-type luciferase gene obtained in the manner as described above is introduced in a usual manner into vectors such as bacteriophage, cosmid, or plasmid used for transforming prokaryotic or eukaryotic cells, and these vectors can be used to transform or transduce hosts compatible therewith. The hosts herein used include microorganisms belonging to the genus Escherichia, for example *E. coli* JM101 (ATCC33875), *E. coli* DH1 (ATCC33849), *E. coli* HB101 (ATCC33694), *E. coli* XL1-blue (purchased from Funakoshi K. K.) etc., and if these microorganisms are selected, they are transformed by the Hanahan method (DNA cloning, 1, 109–135 (1985)) etc. or transduced by the method described in Molecular Cloning, pages 256–268, Cold Spring Harbor Laboratory (1982) etc. so that transformed or transduced microorganisms can be obtained.

The resulting strain is screened for a strain having the ability to produce the mutant-type luciferase, whereby the desired transformed or transduced microorganism, i.e. the strain having the ability to produce the mutant-type luciferase by recombinant DNA having the mutant-type luciferase gene inserted into vector DNA, can be obtained. For purification of the novel recombinant DNA from the strain thus obtained, Current Protocols in Molecular Biology (Wiley Interscience, 1989) unit 1.7 etc. can be used. From the recombinant DNA thus obtained, DNA containing the mutant-type luciferase gene can be obtained for example by allowing an restriction enzyme such as EcoRI to act on said plasmid DNA at a temperature of 30 to 40° C., preferably 37° C. or thereabout, for 1 to 24 hours, preferably 2 hours or thereabout and then subjecting the reaction solution to agarose gel electrophoresis (Molecular Cloning, page 150, Cold Spring Harbor Laboratory (1982)).

Then, the process for producing the mutant-type luciferase of the present invention is described. The mutant-type luciferase of the present invention is obtained by culturing the transformed or transduced microorganism thus obtained and then purifying luciferase from the resulting culture. Although the microorganism may be cultured in a conventional solid medium, it is preferable to employ a liquid medium for culture.

The medium for use in culturing the above strain includes those containing at least one inorganic salts such as sodium chloride, potassium dihydrogen phosphate, dipotassium hydrogen phosphate, magnesium sulfate, magnesium chloride, ferric chloride, ferric sulfate, manganese sulfate etc. added to at least one nitrogen source such as yeast extract, trypton, peptone, meat extract, corn steep liquor, exudate of soybean or wheat bran, etc., and if necessary a suitable amount of sugars (or carbohydrates), vitamins etc. may be added to it.

The initial pH of the medium is preferably adjusted within pH 7 to 9. The microorganism is cultured at 30 to 42° C., preferably about 37° C., for 4 to 24 hours, preferably 6 to 20 hours, preferably using submerged aeration culture, shake culture, or stationary culture. For recovery of the mutant-type luciferase from the culture, conventional enzyme purification means can be used. For example, the microorganism is disrupted in a usual manner by ultrasonication or grinding, or the present enzyme is extracted with a lytic enzyme such as lysozyme etc., or the microorganism is autolyzed in the presence of toluene optionally under shaking to release the present enzyme therefrom.

Then, this solution is filtered, centrifuged etc. to remove insolubles, and if necessary, nucleic acid is removed by adding streptomycin sulfate, protamine sulfate, manganese sulfate etc. The solution is then fractionated with ammonium sulfate, alcohol, acetone etc. and the precipitate is recovered whereby a crude enzyme solution is obtained. The crude enzyme solution is subjected to various kinds of chromatography, electrophoresis etc. to give a purified enzyme preparation. For example, methods such as gel filtration using Sephadex, Ultrogel, Bio-Gel etc., adsorption-elution using ion exchangers, electrophoresis using polyacrylamide gel etc., adsorption-elution using hydroxyapatite, sedimentation such as sucrose density-gradient centrifugation etc., affinity chromatography and fractionation using molecular sieve membrane, hollow fiber membrane etc. can be suitably selected or combined to give the purified enzyme preparation.

Whether the purified mutant-type luciferase has the amino acid sequence with the desired mutation or not can be confirmed by conventional amino acid analysis such as automatic amino acid sequencing by the Edman degradation etc.

According to the present invention, there can be provided luciferase excellent in thermostability etc. and with high catalytic efficiency.

EXAMPLE 1

Figure 1:
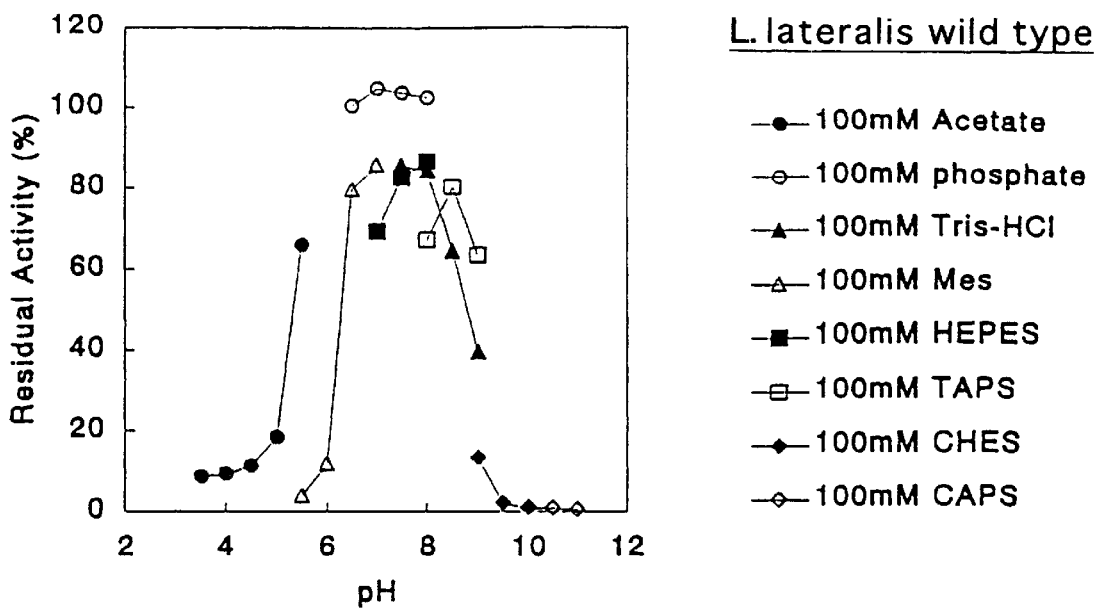
FIG. 1 shows the residual activity of the purified preparation (HLKI luciferase) after treatment in various buffers compared with that of wild-type.
Figure 1:
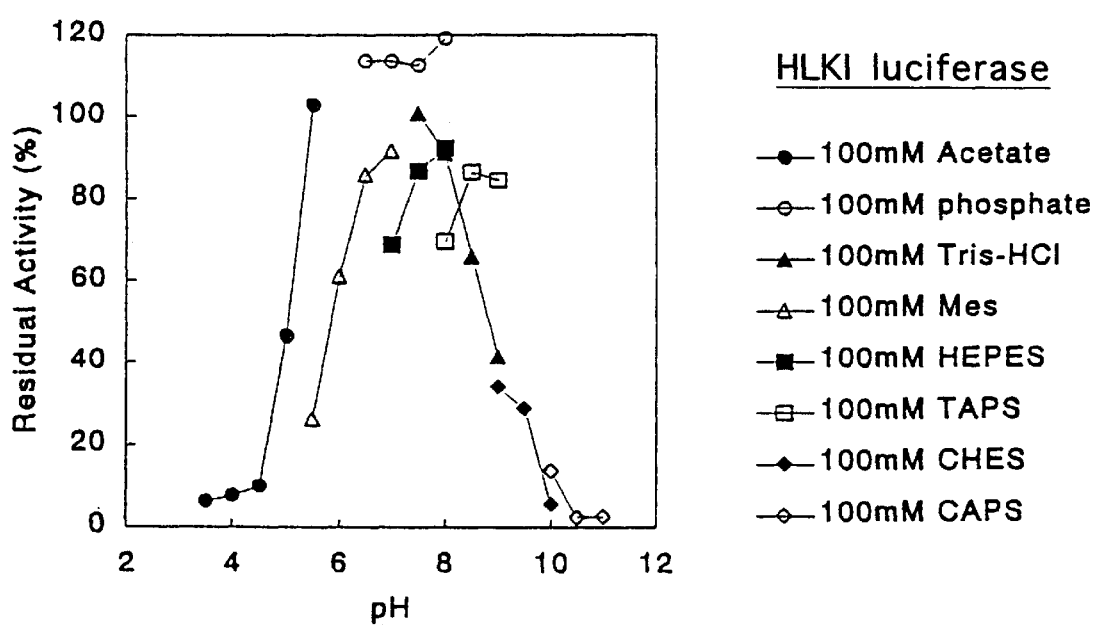

10 $\mu$g plasmid pT3/T7-LUC (obtained from Clontech) for expression of luciferase derived from an American firefly (*Photinus pyralis*) was added to 50 $\mu$ 1 restriction enzyme buffer K [20 mM Tris-HCl (pH 8.5), 10 mM MgCl$_2$, 100 mM KCl, 1 mM dithiothreitol] and then cleaved with 20 U each of restriction enzymes SphI and SmaI (Takara Shuzo Co., Ltd.) at 37° C. for 2 hours. This reaction solution was subjected to 0.8% low-melting agarose gel electrophoresis, and a gel containing an about 1.1-kb DNA fragment containing a C-terminal portion of a luciferase gene derived from Photinus pyralis was cut off and then molten by heating at 65° C. for 5 minutes. To the molten gel was added a 2-fold volume of TE buffer [10 mM Tris-HCl (pH 8.0), 0.5 mM EDTA], and after an equal volume of phenol saturated with TE buffer was added thereto, the mixture was stirred. After centrifugation at 12,000 r.p.m. for 15 minutes, the aqueous layer was recovered and then precipitated with a 2-fold volume of cold ethanol to recover the DNA fragment containing the C-terminal portion of the luciferase gene derived from *Photinus pyralis*.

Separately, synthetic DNAs (SEQ ID NO:1, CTC TAG CAT GCG AAA ATC TAG; SEQ ID NO:2, CTG CAG GCC TGC AAG CTT GG) [prepared by System 1 Plus DNA synthesizer, Beckman] was added to plasmid pGLf37 (described in Japanese Patent Laid-Open Publication No. 244,942/1993) for expression of luciferase derived from Genji firefly (*Luciola cruciata*), and polymerase chain reaction (PCR) was carried out as follows. 50 $\mu$ 1 PCR reaction solution contained 20 $\mu$g plasmid pGLf37, 50 pmol each of the synthetic DNAs, 120 mM Tris-HCl (pH 8.0), 6 mM (NH$_4$)$_2$SO$_4$, 10 mM KCl, 2.5 mM MgSO$_4$, 0.1% Triton X-100, 0.001% BSA, 0.2 mM each of dATP, dGTP, dCTP and dTTP, and 2.5 U of KOD DNA polymerase (Toyobo Co., Ltd.). This mixture was subjected to 25 cycles of PCR, each cycle consisting of incubation at 98° C. for 15 seconds, 65° C. for 2 seconds and 74° C. for 30 seconds in Perkin-Elmer Thermal Cycler PJ2000. To the reaction mixture was added an equal volume of phenol saturated with TE buffer, and the mixture was stirred. After centrifugation at 12,000 r.p.m. for 15 minutes, the aqueous layer was recovered and then precipitated with a 2-fold volume of cold ethanol to recover the DNA fragment. It was dissolved again in TE buffer, then cleaved with SphI and subjected to low-melting agarose gel electrophoresis to recover an about 3.4-kbp DNA fragment containing an N-terminal portion of the luciferase gene derived from *Luciola cruciata*.

50 ng of the above SphI-SmaI fragment from pT3/T7-LUC and 50 ng of the above SphI-cleaved fragment from pGLf37 were incubated at 15° C. for 16 hours in 20 $\mu$l DNA ligase buffer in the presence of 300 U of T4 DNA ligase. The reaction mixture was used to transform *E. coli* JM109 (Toyobo Co., Ltd.) by the Hana-han method [DNA Cloning, 1, 109–135 (1985)], and ampicillin-resistant colonies were selected. A plasmid was removed from the formed colonies by the alkali-SDS method, and the structure of the plasmid was confirmed. This plasmid was subjected to reaction with a dye primer tuck sequencing kit (Applied Biosystems) and analyzed by electrophoresis with an ABI 373A DNA sequencer (Applied Biosystems) to determine its nucleotide sequence. The determined nucleotide sequence is shown in SEQ ID NO:6, and the amino acid sequence of a polypeptide translated from said nucleotide sequence is shown in SEQ ID NO:5. The plasmid thus obtained was designated pGA1.

Plasmid pGA1 was used to transform *E. coli* JM109 in the manner described above to give *E. coli* JM109 (pGA1). *E. coli* JM109 (pGA1) was deposited as FERM BP-5990 with the National Institute of Bioscience and Human-Technology, Agency of Industrial Science and Technology, Japan.

*E. coli* JM109 (pGA1) was inoculated on an LB-amp agar plate [1% (W/V) Bacto-trypton, 0.5% (W/V) yeast extract, 0.5% (W/V) NaCl, (50 $\mu$g/ml) ampicillin and 1.4% (W/V) agar] and cultured at 37° C. The colony microorganisms appearing 16 hours thereafter were inoculated into 10 ml of an LB-amp medium [1% (W/V) Bacto-trypton, 0.5% (W/V) yeast extract, 0.5% (W/V) NaCl and (50 $\mu$g/ml) ampicillin] and cultured at 37° C. for 18 hours under shaking. This culture, 10 ml, was inoculated into 2 L of the above LB-amp medium and cultured at 30° C. for 6 hours under shaking and then centrifuged at 8,000 r.p.m. for 10 minutes to give 30 g wet microbial pellet. The recovered microorganism was suspended in 20 ml buffer consisting of 0.1 M KH$_2$PO$_4$ (pH 7.8), 2 mM EDTA, 1 mM dithiothreitol and 0.2 mg/ml protamine sulfate, and 2 ml of 10 mg/ml lysozyme solution was further added thereto and the mixture was allowed to stand on ice for 15 minutes.

Then, this suspension was frozen in an ethanol/dry ice bath and then allowed to stand at a temperature of 25° C. until it was completely thawed. Further, it was centrifuged at 12,000 r.p.m. for 5 minutes whereby 20 ml crude enzyme was obtained as the supernatant. The crude enzyme solution thus obtained was purified according to the method described in Japanese Patent Laid-Open Publication 141592/1989, and the purified enzyme was designated GA1 luciferase. The Km value of this purified preparation for the substrate ATP was determined. The peak of the emission of light generated by use of the enzyme with the concentration of ATP varying from 0 to 2 mM in a solution containing 50 mM HEPES (pH 7.5), 0.2 mM luciferin and 10 mM MgSO$_4$ was measured in Luminometer ML3000 (Dynatech) and the result is shown in the table 1 below. The thus determined affinity of the GA1 luciferase for ATP was about 5.73-fold higher than the wild-type *Photinus pyralis* luciferase and about 11.4-fold higher than the wild-type *Luciola cruciata* luciferase. This improvement in the affinity of the GA1 luciferase for ATP as compared with that of the wild-type luciferases revealed that the GA1 luciferase is a highly useful enzyme.

TABLE 1

|  | Km (mM) |
| --- | --- |
| *Photinus pyralis* luciferase | 0.152 |
| *Luciola cruciata* luciferase | 0.301 |
| GA1 luciferase | 0.0265 |

EXAMPLE 2

10μ g plasmid pT3/T7-LUC (obtained from Clontech) for expression of luciferase derived from an American firefly (*Photinus pyralis*) was added to 50 μ l buffer H [50 mM Tris-HCl (pH 7.5), 10 mM $MgCl_2$, 100 mM NaCl, 1 mM dithiothreitol] and then cleaved with 20 U each of restriction enzymes EcoRV and SalI (Takara Shuzo Co., Ltd.) at 37° C. for 2 hours. This reaction solution was subjected to 0.8% low-melting agarose gel electrophoresis, and a gel containing an about 0.5-kb DNA fragment containing a C-terminal portion of a luciferase gene derived from *Photinus pyralis* was cut off and then molten by heating at 65° C. for 5 minutes. To the molten gel was added a 2-fold volume of TE buffer [10 mM Tris-HCl (pH 8.0), 0.5 mM EDTA], and after an equal volume of phenol saturated with TE buffer was added thereto, the mixture was stirred. After centrifugation (12,000 r.p.m. for 15 minutes), the aqueous layer was recovered and then precipitated with a 2-fold volume of cold ethanol to recover a DNA fragment containing a region coding for the C-terminal of luciferase from *Photinus pyralis*.

Separately, synthetic DNAs (SEQ ID NO:3, ATC CTT TGT ATT TGA TTA AAG; SEQ ID NO:4, TCT AGA GTC GAC CTG CAG GC) [prepared by System 1 Plus DNA synthesizer, Beckman] was added to plasmid pGLf37 T-M-2 (described in Japanese Patent Laid-Open Publication No. 244,942/1993) for expression of thermostable luciferase derived from Genji firefly (*Luciola cruciata*), and polymerase chain reaction (PCR) was carried out as follows. 50 μ l PCR reaction solution contained 20 μ g plasmid pGLf37 T-M-2, 50 pmol each of the synthetic DNAs, 120 mM Tris-HCl (pH 8.0), 6 mM $(NH_4)_2SO_4$, 10 mM KCl, 2.5 mM $MgSO_4$, 0.1% Triton X-100, 0.001% BSA, 0.2 mM each of dATP, dGTP, dCTP and dTTP, and 2.5 U of KOD DNA polymerase (Toyobo Co., Ltd.). This mixture was subjected to 25 cycles of PCR, each cycle consisting of incubation at 98° C. for 15 seconds, 65° C. for 2 seconds and 74° C. for 30 seconds in Perkin-Elmer Thermal Cycler PJ2000. To the reaction mixture was added an equal volume of phenol saturated with TE buffer, and the mixture was stirred. After centrifugation (12,000 r.p.m. for 15 minutes), the aqueous layer was recovered and then precipitated with a 2-fold volume of cold ethanol to recover the DNA fragment. It was dissolved again in TE buffer, then cleaved with SalI and subjected to low-melting agarose gel electrophoresis to recover a DNA fragment containing a region coding for the N-terminal of luciferase derived from *Luciola cruciata*. In this region, a thermostable mutation (Thr217Ile) derived from pGLf37 T-M-2 was contained.

50 ng of the above about 0.5-kbp EcoRV-SalI fragment derived from pT3/T7-LUC and 50 ng of the above about 4-kbp SalI-cleaved fragment derived from pGLf37 T-M-2 were incubated at 15° C. for 16 hours in 20 μ l DNA ligase buffer in the presence of 300 U of T4 DNA ligase. The reaction mixture was used to transform *E. coli* JM109 (Toyobo Co., Ltd.) by the Hana-han method [DNA Cloning, 1, 109–135 (1985)], and ampicillin-resistant colonies were selected.

A plasmid was removed from the formed colonies by the alkali-SDS method, This plasmid was subjected to reaction with a dye primer tuck sequencing kit (Applied Biosystems) and analyzed by electrophoresis with an ABI 373A DNA sequencer (Applied Biosystems) to determine its nucleotide sequence. The determined nucleotide sequence is shown in SEQ ID NO:8, and the amino acid sequence of a polypeptide translated from said nucleotide sequence is shown in SEQ ID NO:7. The plasmid thus obtained was designated pGGA1.

Plasmid pGGA1 was used to transform *E. coli* JM109 in the manner described above to give *E. coli* JM109 (pGGA1). *E. coli* JM109 (pGGA1) was deposited as FERM BP-5989 with the National Institute of Bioscience and Human-Technology, Agency of Industrial Science and Technology, Japan.

*E. coli* JM109 (pGGA1) was inoculated on an LB-amp agar plate [1% (W/V) Bacto-trypton, 0.5% (W/V) yeast extract, 0.5% (W/V) NaCl, (50 a g/ml) ampicillin and 1.4% (W/V) agar] and cultured at 37° C. The colonies appearing 16 hours thereafter were cultured at 37° C. for 18 hours under shaking in 10 ml of an LB-amp medium [1% (W/V) Bacto-trypton, 0.5% (W/V) yeast extract, 0.5% (W/V) NaCl and (50 μ g/ml) ampicillin]. This culture, 10 ml, was inoculated into 2 L of the above LB-amp medium and cultured at 30 ° C. for 6 hours under shaking and then centrifuged at 8000 r.p.m. for 10 minutes to give 30 g wet microbial pellet. The recovered microorganism was suspended in 20 ml buffer consisting of 0.1 M $KH_2PO_4$ (pH 7.8), 2 mM EDTA, 1 mM dithiothreitol and 0.2 mg/ml protamine sulfate, and 2 ml of 10 mg/ml lysozyme solution was further added thereto and the mixture was allowed to stand on ice for 15 minutes. Then, this suspension was frozen in an ethanol/dry ice bath and then allowed to stand at a temperature of 25° C. until it was completely thawed. Further, it was centrifuged at 12,000 r.p.m. for 5 minutes whereby 20 ml crude enzyme was obtained as the supernatant. The crude enzyme solution thus obtained was purified according to the method described in Japanese Patent Laid-Open Publication 141592/1989, and the purified enzyme was designated GGA1 luciferase.

The Km value of this purified GGA1 enzyme for the substrate ATP was determined (Table 2). The result indicated that the affinity of the GGA1 luciferase for ATP was about 1.46 fold higher than the wild-type *Photinus pyralis* luciferase and about 2.89-fold higher than the wild-type *Luciola cruciata* luciferase. This improvement in the affinity of the GGA1 luciferase for ATP as compared with that of the wild-type luciferase reveals that the GGA1 luciferases is a very useful enzyme.

TABLE 2

|  | Km (mM) |
| --- | --- |
| *Photinus pyralis* luciferase | 0.152 |
| *Luciola cruciata* luciferase | 0.301 |
| GGA1 luciferase | 0.104 |

This purified enzyme was examined for thermal stability where the remaining activity after treated at 50° C. in 0.05 M potassium phosphate buffer (pH 7.8) with 10% ammonium sulfate saturation was determined. The result indicated that this enzyme maintained 80% or more of the original activity even after treatment at 50° C. for 20 minutes, and it was thus found that the thermal stability of this enzyme has been improved as compared with that of the wild-type *Photinus pyralis* luciferase and the thermostable *Luciola cruciata* luciferase.

EXAMPLE 3

10 μg plasmid pT3/T7-LUC (obtained from Clontech) for expression of luciferase derived from an American firefly (*Photinus pyralis*) was added to 50 μl restriction enzyme buffer H [50 mM Tris-HCl (pH 7.5), 10 mM $MgCl_2$, 100 mM NaCl, 1 mM dithiothreitol] and then cleaved with 20 U of restriction enzyme EcoRV (Takara Shuzo Co., Ltd.) at 37° C. for 2 hours. This reaction solution was subjected to 0.8% low-melting agarose gel electrophoresis, and a gel containing an about 500 bp DNA fragment containing a region coding for the C-terminal of the luciferase from *Photinus pyralis* was cut off and then molten by heating at 65° C. for 5 minutes. To the molten gel was added a 2-fold volume of TE buffer [10 mM Tris-HCl (pH 8.0), 0.5 mM EDTA], and after an equal volume of phenol saturated with TE buffer was added thereto, the mixture was stirred. After centrifugation (12,000 r.p.m. for 15 minutes), the aqueous layer was recovered and then precipitated with a 2-fold volume of cold ethanol to recover the DNA fragment containing a region coding for the C-terminal of the *Photinus pyralis* luciferase Separately, 10 μg plasmid pHLf7–217Leu (Japanese Patent Application Laid-Open Publication No. 244942/93) for expression of luciferase derived from Heike firefly (*Luciola lateralis*) was added to 50 μl restriction enzyme buffer T [33 mM Tris-HCl (pH 7.9), 10 mM magnesium acetate, 66 mM potassium acetate, 0.5 mM dithiothreitol] and then cleaved with 20 U each of restriction enzymes EcoRV and NaeI (Takara Shuzo Co., Ltd.) at 37° C. for 2 hours. This reaction solution was subjected to 0.8% low-melting agarose gel electrophoresis, and a gel containing an about 4.3 kbp DNA fragment containing the N-terminal of the luciferase from *Luciola lateralis* was cut off and then molten by heating at 65° C. for 5 minutes. To the molten gel was added a 2-fold volume of TE buffer [10 mM Tris-HCl (pH 8.0), 0.5 mM EDTA], and after an equal volume of phenol saturated with TE buffer was added thereto, the mixture was stirred. After centrifugation (12,000 r.p.m. for 15 minutes), the aqueous layer was recovered and then precipitated with a 2-fold volume of cold ethanol to recover the DNA fragment containing a region coding for the N-terminal of the *Luciola lateralis* luciferase.

50 ng of the above EcoRV—EcoRV fragment from pT3/T7-LUC and 50 ng of the above EcoRV-NaeI fragment from pHLf7–217Leu were incubated at 15° C. for 16 hours in 20 μl DNA ligase buffer in the presence of 300 U of T4 DNA ligase. The reaction mixture was used to transform *E. coli* JM 109 by the Hana-han method [DNA Cloning, 1, 109–135 (1985)], and ampicillin-resistant colonies were selected. A crude enzyme was prepared from the selected colonies in the method described in Example 1, and a plasmid was removed by the alkali-SDS method from those having luminescence activity, and the structure of the plasmid was confirmed. This plasmid was subjected to reaction with a dye primer tuck sequencing kit (Applied Biosystems) and analyzed by electrophoresis with an ABI 373A DNA sequencer (Applied Biosystems) to determine its nucleotide sequence (SEQ ID NO:9). The amino acid sequence of a polypeptide estimated to be translated from said nucleotide sequence is shown in SEQ ID NO:10. The plasmid thus obtained was designated pHHA1.

Plasmid pHHA1 was used to transform *E. coli* JM 109 in the above method to give *E. coli* JM 109 (pHHA1). The *E. coli* JM 109 (pHHA1) has been deposited as FERM BP-6203 with the National Institute of Bioscience and Human-Technology, Agency of Industrial Science and Technology, Japan.

Further, its crude enzyme solution was prepared using the method described in Example 1 and the enzyme was purified in a method described in Japanese Patent Application Laid-Open Publication No. 141592/89. The purified enzyme was designated HHA1 luciferase. The affinity of HHA1 luciferase for the substrate ATP was determined. The peak of the emission of light generated by use of the enzyme with the concentration of ATP varying from 0 to 2 mM in a solution containing 50 mM Tricine buffer (pH 7.8), 0.2 mM luciferin and 10 mM $MgSO_4$ was measured in Luminometer ML3000 (Dynatech). The affinity (Km value) of the HHA1 luciferase for ATP was thus determined (Table 3). The affinity of the HHA1 luciferase for ATP was improved as compared with those of the *Photinus pyralis* and *Luciola lateralis* luciferases, indicating that the HHA1 luciferase is a highly useful enzyme.

TABLE 3

|  | Km (mM) |
|---|---|
| *Photinus pyralis* luciferase | 0.161 |
| *Luciola lateralis* luciferase | 0.197 |
| HHA1 luciferase | 0.123 |

EXAMPLE 4

To introduce an arbitrary mutation into the luciferase gene, plasmid pGGA1 described in Example 2 was treated at 65° C. for 2 hours in 0.1 M sodium phosphate buffer (pH 6.0) containing 0.8 M hydroxylamine and 1 mM EDTA according to the method of Kironde et al. [Biochem. J., 25, 421–426 (1989)]. The plasmid thus subjected to mutagenesis was desalted by passing it through a G60 DNA grade Nick column (Pharmacia), and then *E. coli* JM 109 was transformed with this plasmid.

The resulting transformant was inoculated on an LB-amp plate [1.0% (W/V) Bacto-trypton, 0.5% (W/V) yeast extract, 0.5% (W/V) NaCl, 1.5% (W/V) agar and 50 μg/ml ampicillin] and cultured at 37° C. for 12 hours. The resulting colonies were transferred onto a nitrocellulose filter, and said filter was immersed in 0.1 M sodium citrate buffer (pH 5.0) containing 0.5 mM luciferin [Wood & DeLuca, Anal. Biochem., 161, 501–507 (1987)]. The emission of light from said colonies was monitored, and 3 strains with raised emission could be obtained. These strains were designated *E. coli* JM 109 (pGGA2–1), *E. coli* JM 109 (pGGA1–4) and *E. coli* JM 109 (pGGA2–4), respectively. The *E. coli* JM 109 (pGGA2–1), *E. coli* JM 109 (pGGA1–4) and *E. coli* JM 109 (pGGA2–4) thus obtained have been deposited respectively as FERM BP-6206, FERM BP-6205 and FERM BP-6204 with the National Institute of Bioscience and Human-Technology, Agency of Industrial Science and Technology. Plasmids were removed from these strains by alkali-SDS method. These plasmids were subjected to reaction with a dye primer tuck sequencing kit (Applied Biosystems) and analyzed by electrophoresis with an ABI 373A DNA sequencer (Applied Biosystems) to determine their mutation sites (Table 4).

TABLE 4

| | Position and Nucleotide Change | Position and Amino Acid Change |
|---|---|---|
| E. coli JM 109 (pGGA2-1) | 656-position C → T | 219-position Thr → Ile |
| E. coli JM 109 (pGGA1-4) | 868-position G → A | 290-position Val → Ile |
| E. coli JM 109 (pGGA2-4) | 715-position G → A | 239-position Val → Ile |

From the E. coli JM 109 (pGGA2-1), E. coli JM 109 (pGGA1-4), E. coli JM 109 (pGGA2-4), their crude enzyme solutions were extracted by the method described in Example 1, and these mutant enzymes were purified in the method described in Japanese Patent Laid-Open Publication No. 141592/1989. The purified enzymes were designated GGA1 T219I luciferase, GGA1 V290I luciferase and GGA1 V239I luciferase, respectively. These enzymes were determined for their catalyst efficiency (Vmax/Km) toward the substrate ATP. The luminescent reaction was carried out by mixing, with each enzyme, a substrate mixture containing ATP at concentrations varying from 0 to $1.0 \times 10^{-3}$ mM in 50 mM Tricine buffer (pH 7.8), 2.0 mM luciferin and 10 mM $MgSO_4$. The emission of light from 5 seconds to 15 seconds after initiation of the reaction was integrated in Luminometer ML3000 (Dynatech) to determine catalytic efficiency (Vmax/Km). As shown in the table below, it was confirmed that as compared with the GGA1 luciferase, catalytic efficiency was improved by mutating each of the amino acids at the 219-, 290-, and 239-positions.

TABLE 5

| | Vmax/Km (x $10^9$ RLU/mg) |
|---|---|
| GGA1 luciferase | 1.22 |
| GGA1 T219I luciferase | 2.16 |
| GGA1 V290I luciferase | 1.70 |
| GGA1 V239I luciferase | 1.58 |

EXAMPLE 5

To obtain mutant luciferase with improvements in pH stability, an arbitrary mutation was introduced to the wild-type luciferase gene.

For mutation, PCR was conducted in the presence of 0.5 mM $Mn^{2+}$ reported to cause frequent mutations (A Journal of Methods in Cell and Molecular Biology, Vol. 1, No. 1 (1989), pp. 11–15) where plasmid pHLf7 for expression of luciferase derived from Heike firefly (*Luciola lateralis*) (described in Japanese Patent Application Laid-open Publication No. 171189/90) was used as a template and oligonucleotides shown in SEQ ID NOS: 11 (AGAGATCCAA TTTATGGAAA C) and 12 (AGCGTGAGAA AATCT-GATCA C) were used as primers. After reaction, the reaction solution was precipitated with a 2-fold volume of cold ethanol. The resulting DNA was dissolved again in TE buffer, 10 U of T4 polynucleotide kinase (Takara Shuzo Co., Ltd.) in T4 polynucleotide kinase buffer was then added, and the mixture was reacted at 37° C. for 30 minutes. This reaction solution was then subjected to 0.8% low-melting agarose gel electrophoresis, and a gel containing an about 5 kbp DNA fragment was cut off and then molten by heating at 65° C. for 5 minutes. To the molten gel was added a 2-fold volume of TE buffer [10 mM Tris-HCl (pH 8.0), 0.5 mM EDTA], and after an equal volume of phenol saturated with TE buffer was added thereto, the mixture was stirred. After centrifugation (12,000 r.p.m. for 15 minutes), the aqueous layer was recovered and then precipitated with a 2-fold volume of cold ethanol to recover the about 5 kbp DNA fragment. 50 ng of the about 5 kbp DNA fragment thus recovered was incubated at 15° C. for 16 hours in 20 $\mu$l DNA ligase buffer in the presence of 10 U of T4 DNA ligase (Toyobo). The reaction mixture was used to transform E. coli JM 109 by the Hana-han method [DNA Cloning, 1, 109–135 (1985)], and ampicillin-resistant colonies were selected on an LB+Amp plate [1.0% (W/V) Bacto-trypton, 0.5% (W/V) yeast extract, 0.5% (W/V) NaCl, 1.4% (W/V) Bacto-agar and 50 $\mu$ g/ml ampicillin].

The resulting colonies were cultured in LB medium, and their crude enzyme was prepared by the method described in Example 1. The crude enzyme was treated in 100 mM acetate buffer (pH 5.5) at 25° C. for 22 hours to screen a strain with the activity not lowered. As a result, in contrast to the wild-type losing the activity to a level of about 70% or less, a strain hardly losing the activity was obtained. A plasmid was removed from this strain by the alkali-SDS method, subjected to reaction with a dye primer tuck sequencing kit (Applied Biosystems), and analyzed by electrophoresis with an ABI 373A DNA sequencer (Applied Biosystems) to determine its nucleotide sequence (SEQ ID NO:13). The amino acid sequence deduced from this nucleotide sequence is shown in SEQ ID NO:14. The plasmid thus obtained was designated pHLKI.

Plasmid pHLKI was used to transform E. coli JM 109 in the method described above. The resulting E. coli JM 109 (pHLKI) has been deposited as FERM BP-6347 with the National Institute of Bioscience and Human-Technology, Agency of Industrial Science and Technology, Japan.

It was cultured in LB medium, its crude enzyme solution was then prepared by the method described in Example 1 and the enzyme was purified in a method described in Japanese Patent Application Laid-Open Publication No. 141592/89. This purified preparation (HLKI luciferase) was treated in various buffers at 25° C. for 22 hours and measured for its residual activity (FIG. 1). As can be seen from FIG. 1, the resulting HLKI luciferase exhibits higher residual activity in the broad range of pH 5.0 to 10.0 than that of the wild strain. As a specific example, its residual activity in the ranges pH 5.0 to 6.0 and pH 9.0 to 10.0 is shown in Table 6.

In Table 6, HLKI luciferase exhibited 2.5-fold or more higher residual activity in 100 mM acetate buffer, pH 5.0 in the acid range than the *Luciola lateralis* wild-type counterpart. Further, it exhibited 6-fold or more higher residual activity in 100 mM Mes buffer, pH 5.5. In the alkali range, HLKI luciferase exhibited 2.5-fold or more higher residual activity in 100 mM CHES buffer, pH 9.0 and 13-fold or more higher residual activity in 100 mM CHES buffer, pH 9.5 respectively than that of the *Luciola lateralis* wild-type counterpart. This comparison between HLKI luciferase and the *Luciola lateralis* wild-type counterpart in the residual activity in buffers at specific pH values indicates that the residual activity is increased in HLKI luciferase.

It is further understood that HLKI luciferase maintains 80% or more residual activity in the range from pH 6.0–6.5 (100 mM Mes buffer) to pH 9.0 (100 mM TAPS buffer), as opposed to the *Luciola lateralis* wild-type counterpart which maintains 80% or more residual activity in the range of pH 6.5 (100 mM Mes buffer) to pH 8.5 (100 mM TAPS buffer). This indicates that the pH range in which HLKI luciferase maintains 80% or more residual activity is broader than that of the *Luciola lateralis* wild-type counterpart.

These results indicate that HLKI luciferase has higher pH stability than the enzyme of the wild strain, and according to this property, it can also be reacted in the pH range not applicable to the enzyme of the wild-type counterpart, so it is extremely useful.

TABLE 6

|  | Acid range | | | | Alkali range | | |
| --- | --- | --- | --- | --- | --- | --- | --- |
|  | Acetate buffer | | Mes buffer | | CHES buffer | | CAPS buffer |
| pH | 5.0 | 5.5 | 5.5 | 6.0 | 9.0 | 9.5 | 10.0 |
| *L. lateralis* wild type | 18.0 | 66.0 | 3.90 | 12.0 | 13.3 | 2.10 | 0.800 |
| HLKI luciferase | 46.0 | 102 | 26.3 | 61.0 | 33.9 | 28.8 | 13.7 |

What is claimed is:

1. A bioluminescent protein having firefly luciferase activity and having a mutation in an amino acid residue corresponding to the 219-position of the *Luciola cruciata* luciferase.

2. The bioluminescent protein of claim 1, wherein the amino C acid residue corresponding to the 219-position of the *Luciola cruciata* luciferase is an isoleucine residue.

3. A bioluminescent protein having firefly luciferase activity and having a mutation in an amino acid residue corresponding to the 290-position of the *Luciola cruciata* luciferase.

4. The bioluminescent protein of claim 3, wherein the amino C acid residue corresponding to the 290-position of the *Luciola cruciata* luciferase is an isoleucine residue.

5. A bioluminescent protein having firefly luciferase activity, wherein the bioluminescent protein of claim 1 is fused to at least one other bioluminescent protein having firefly luciferase activity.

6. The bioluminescent protein of claim 5, wherein said other bioluminescent protein having firefly luciferase activity is a luciferase from Heike firefly (*Luciola lateralis*), American firefly (*Photinus pyralis*) or Genji firefly (*Luciola cruciata*).

7. A bioluminescent protein having firefly luciferase activity, wherein the bioluminescent protein of claim 2 is fused to at least one other bioluminescent protein having firefly luciferase activity.

8. The bioluminescent protein of claim 7, wherein said other bioluminescent protein having firefly luciferase activity is a luciferase from Heike firefly (*Luciola lateralis*), American firefly (*Photinus pyralis*) or Genji firefly (*Luciola cruciata*).

9. A bioluminescent protein having firefly luciferase activity, wherein the bioluminescent protein of claim 3 is fused to at least one other bioluminescent protein having firefly luciferase activity.

10. The bioluminescent protein of claim 9, wherein said other bioluminescent protein having firefly luciferase activity is a luciferase from Heike firefly (*Luciola lateralis*), American firefly (*Photinus pyralis*) or Genji firefly (*Luciola cruciata*).

11. A bioluminescent protein having firefly luciferase activity, wherein the bioluminescent protein of claim 4 fused to at least one other bioluminescent protein having firefly luciferase activity.

12. The bioluminescent protein of claim 11, wherein said other bioluminescent protein having firefly luciferase activity is a luciferase from Heike firefly (*Luciola lateralis*), American firefly (*Photinus pyralis*) or Genji firefly (*Luciola cruciata*).

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

CTCTAGCATG CGAAAATCTA G      21

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:2:

CTGCAGGCCT GCAAGCTTGG      20

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:3:

ATCCTTTGTA TTTGATTAAA G      21

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single (D) TOPOLOGY: linear (ii) MOLECULE TYPE: other nucleic acid (xi) SEQUENCE DESCRIPTION: SEQ ID NO:4:

TCTAGAGTCG ACCTGCAGGC                                                    20

(2) INFORMATION FOR SEQ ID NO:5:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Luciola cruciata and Phontinus pyralis (xi) SEQUENCE DESCRIPTION: SEQ ID NO:5:

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
    210                 215                 220

Arg Asp Pro Ile Phe Gly Asn Gln Ile Ile Pro Asp Thr Ala Ile Leu
225                 230                 235                 240

Ser Val Val Pro Phe His His Gly Phe Gly Met Phe Thr Thr Leu Gly
                245                 250                 255

Tyr Leu Ile Cys Gly Phe Arg Val Val Leu Met Tyr Arg Phe Glu Glu
            260                 265                 270

Glu Leu Phe Leu Arg Ser Leu Gln Asp Tyr Lys Ile Gln Ser Ala Leu
        275                 280                 285

Leu Val Pro Thr Leu Phe Ser Phe Phe Ala Lys Ser Thr Leu Ile Asp

```
                290             295             300
Lys Tyr Asp Leu Ser Asn Leu His Glu Ile Ala Ser Gly Gly Ala Pro
305             310             315             320
Leu Ser Lys Glu Val Gly Glu Ala Val Ala Lys Arg Phe His Leu Pro
            325             330             335
Gly Ile Arg Gln Gly Tyr Gly Leu Thr Glu Thr Thr Ser Ala Ile Leu
            340             345             350
Ile Thr Pro Glu Gly Asp Asp Lys Pro Gly Ala Val Gly Lys Val Val
            355             360             365
Pro Phe Phe Glu Ala Lys Val Val Asp Leu Asp Thr Gly Lys Thr Leu
370             375             380
Gly Val Asn Gln Arg Gly Glu Leu Cys Val Arg Gly Pro Met Ile Met
385             390             395             400
Ser Gly Tyr Val Asn Asn Pro Glu Ala Thr Asn Ala Leu Ile Asp Lys
            405             410             415
Asp Gly Trp Leu His Ser Gly Asp Ile Ala Tyr Trp Asp Glu Asp Glu
            420             425             430
His Phe Phe Ile Val Asp Arg Leu Lys Ser Leu Ile Lys Tyr Lys Gly
            435             440             445
Tyr Gln Val Ala Pro Ala Glu Leu Glu Ser Ile Leu Leu Gln His Pro
450             455             460
Asn Ile Phe Asp Ala Gly Val Ala Gly Leu Pro Asp Asp Asp Ala Gly
465             470             475             480
Glu Leu Pro Ala Ala Val Val Val Leu Glu His Gly Lys Thr Met Thr
            485             490             495
Glu Lys Glu Ile Val Asp Tyr Val Ala Ser Gln Val Thr Thr Ala Lys
            500             505             510
Lys Leu Arg Gly Gly Val Val Phe Val Asp Glu Val Pro Lys Gly Leu
            515             520             525
Thr Gly Lys Leu Asp Ala Arg Lys Ile Arg Glu Ile Leu Ile Lys Ala
530             535             540
Lys Lys Gly Gly Lys Ser Lys Leu
545             550

(2) INFORMATION FOR SEQ ID NO:6:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Luciola cruciata and Phontinus pyralis (xi) SEQUENCE DESCRIPTION: SEQ ID NO:6:

ATGGAAAACA TGGAAAACGA TGAAAATATT GTAGTTGGAC CTAAACCGTT TTACCCTATC        60

GAAGAGGGAT CTGCTGGAAC ACAATTACGC AAATACATGG AGCGATATGC AAAACTTGGC      120

GCAATTGCTT TTACAAATGC AGTTACTGGT GTTGATTATT CTTACGCCGA ATACTTGGAG      180

AAATCATGTT GTCTAGGAAA AGCTTTGCAA AATTATGGTT TGGTTGTTGA TGGCAGAATT      240

GCGTTATGCA GTGAAAACTG TGAAGAATTT TTTATTCCTG TAATAGCGG  ACTGTTTATA      300

GGTGTAGGTG TTGCACCCAC TAATGAGATT TACACTTTAC GTGAACTGGT TCACAGTTTA      360

GGTATCTCTA AACCAACAAT TGTATTTAGT TCTAAAAAAG CTTAGATAA  AGTTATAACA      420
```

-continued

```
GTACAGAAAA CAGTAACTAC TATTAAAACC ATTGTTATAC TAGATAGCAA AGTTGATTAT    480

CGAGGATATC AATGTCTGGA CACCTTTATA AAAAGAAACA CTCCACCAGG TTTTCAAGCA    540

TCCAGTTTCA AAACTGTGGA AGTTGACCGT AAAGAACAAG TTGCTCTTAT AATGAACTCT    600

TCGGGTTCTA CCGGTTTGCC AAAAGGCGTA CAACTTACTC ACGAAAATAC AGTCACTAGA    660

TTTTCGCATG CCAGAGATCC TATTTTTGGC AATCAAATCA TTCCGGATAC TGCGATTTTA    720

AGTGTTGTTC CATTCCATCA CGGTTTTGGA ATGTTTACTA CACTCGGATA TTTGATATGT    780

GGATTTCGAG TCGTCTTAAT GTATAGATTT GAAGAAGAGC TGTTTTTACG ATCCCTTCAG    840

GATTACAAAA TTCAAAGTGC GTTGCTAGTA CCAACCCTAT TTTCATTCTT CGCCAAAAGC    900

ACTCTGATTG ACAAATACGA TTTATCTAAT TTACACGAAA TTGCTTCTGG GGGCGCACCT    960

CTTTCGAAAG AAGTCGGGGA AGCGGTTGCA AAACGCTTCC ATCTTCCAGG GATACGACAA   1020

GGATATGGGC TCACTGAGAC TACATCAGCT ATTCTGATTA CACCCGAGGG GGATGATAAA   1080

CCGGGCGCGG TCGGTAAAGT TGTTCCATTT TTTGAAGCGA AGGTTGTGGA TCTGGATACC   1140

GGGAAAACGC TGGGCGTTAA TCAGAGAGGC GAATTATGTG TCAGAGGACC TATGATTATG   1200

TCCGGTTATG TAAACAATCC GGAAGCGACC AACGCCTTGA TTGACAAGGA TGGATGGCTA   1260

CATTCTGGAG ACATAGCTTA CTGGGACGAA GACGAACACT TCTTCATAGT TGACCGCTTG   1320

AAGTCTTTAA TTAAATACAA AGGATATCAG GTGGCCCCCG CTGAATTGGA ATCGATATTG   1380

TTACAACACC CCAACATCTT CGACGCGGGC GTGGCAGGTC TTCCCGACGA TGACGCCGGT   1440

GAACTTCCCG CCGCCGTTGT TGTTTTGGAG CACGGAAAGA CGATGACGGA AAAAGAGATC   1500

GTGGATTACG TCGCCAGTCA AGTAACAACC GCGAAAAAGT TGCGCGGAGG AGTTGTGTTT   1560

GTGGACGAAG TACCGAAAGG TCTTACCGGA AAACTCGACG CAAGAAAAAT CAGAGAGATC   1620

CTCATAAAGG CCAAGAAGGG CGGAAAGTCC AAATTG                             1656
```

(2) INFORMATION FOR SEQ ID NO:7:

(i) SEQUENCE CHARACTERISTICS:
  (A) LENGTH: 552 amino acids
  (B) TYPE: amino acid
  (C) STRANDEDNESS: single
  (D) TOPOLOGY: linear (ii) MOLECULE TYPE: peptide (vi) ORIGINAL SOURCE:
  (A) ORGANISM: Luciola cruciata and Phontius pyralis (xi) SEQUENCE DESCRIPTION: SEQ ID NO:7:

```
Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110
```

```
Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
130                     135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ile Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Ser Leu
    370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
                405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Ala Pro Ala Glu Leu Glu Ser Ile Leu Leu Gln His Pro
    450                 455                 460

Asn Ile Phe Asp Ala Gly Val Ala Gly Leu Pro Asp Asp Asp Ala Gly
465                 470                 475                 480

Glu Leu Pro Ala Ala Val Val Leu Glu His Gly Lys Thr Met Thr
                485                 490                 495

Glu Lys Glu Ile Val Asp Tyr Val Ala Ser Gln Val Thr Thr Ala Lys
            500                 505                 510

Lys Leu Arg Gly Gly Val Val Phe Val Asp Glu Val Pro Lys Gly Leu
        515                 520                 525
```

```
Thr Gly Lys Leu Asp Ala Arg Lys Ile Arg Glu Ile Leu Ile Lys Ala
    530                 535                 540

Lys Lys Gly Gly Lys Ser Lys Leu
545                 550
```

(2) INFORMATION FOR SEQ ID NO:8:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Luciola cruciata and Phontinus pyralis (xi) SEQUENCE DESCRIPTION: SEQ ID NO:8:

```
ATGGAAAACA TGGAAAACGA TGAAAATATT GTAGTTGGAC CTAAACCGTT TTACCCTATC      60
GAAGAGGGAT CTGCTGGAAC ACAATTACGC AAATACATGG AGCGATATGC AAAACTTGGC     120
GCAATTGCTT TTACAAATGC AGTTACTGGT GTTGATTATT CTTACGCCGA ATACTTGGAG     180
AAATCATGTT GTCTAGGAAA AGCTTTGCAA AATTATGGTT TGGTTGTTGA TGGCAGAATT     240
GCGTTATGCA GTGAAAACTG TGAAGAATTT TTTATTCCTG TAATAGCCGG ACTGTTTATA     300
GGTGTAGGTG TTGCACCCAC TAATGAGATT TACACTTTAC GTGAACTGGT TCACAGTTTA     360
GGTATCTCTA AACCAACAAT TGTATTTAGT TCTAAAAAAG GCTTAGATAA AGTTATAACA     420
GTACAGAAAA CAGTAACTAC TATTAAAACC ATTGTTATAC TAGATAGCAA AGTTGATTAT     480
CGAGGATATC AATGTCTGGA CACCTTTATA AAAAGAAACA CTCCACCAGG TTTTCAAGCA     540
TCCAGTTTCA AAACTGTGGA AGTTGACCGT AAAGAACAAG TTGCTCTTAT AATGAACTCT     600
TCGGTTCTA CCGGTTTGCC AAAAGGCGTA CAACTTACTC ACGAAAATAT AGTCACTAGA     660
TTTTCTCATG CTAGAGATCC GATTTATGGT AACCAAGTTT CACCAGGCAC CGCTGTTTTA     720
ACTGTCGTTC CATTCCATCA TGGTTTTGGT ATGTTCACTA CTCTAGGGTA TTTAATTTGT     780
GGTTTTCGTG TTGTAATGTT AACAAAATTC GATGAAGAAA CATTTTTAAA AACTCTACAA     840
GATTATAAAT GTACAAGTGT TATTCTTGTA CCGACCTTGT TTGCAATTCT CAACAAAAGT     900
GAATTACTCA ATAAATACGA TTTGTCAAAT TTAGTTGAGA TTGCATCTGG CGGAGCACCT     960
TTATCAAAAG AAGTTGGTGA AGCTGTTGCT AGACGCTTTA ATCTTCCCGG TGTTCGTCAA    1020
GGTTATGGTT TAACAGAAAC AACATCTGCC ATTATTATTA CACCGGAAGG TGACGATAAA    1080
CCAGGAGCTT CTGGAAAAGT CGTGCCGTTG TTTAAAGCAA AAGTTATTGA TCTTGATACT    1140
AAAAAATCTT TAGGTCCTAA CAGACGTGGA GAAGTTTGTG TTAAAGGACC TATGCTTATG    1200
AAAGGTTATG TAAATAATCC AGAAGCAACA AAAGAACTTA TTGACGAAGA AGGTTGGCTG    1260
CACACCGGAG ATATTGGATA TTATGATGAA GAAAAACATT TCTTTATTGT CGATCGTTTG    1320
AAGTCTTTAA TCAAATACAA AGGATATCAG GTGGCCCCCG CTGAATTGGA ATCGATATTG    1380
TTACAACACC CCAACATCTT CGACGCGGGC GTGGCAGGTC TTCCCGACGA TGACGCCGGT    1440
GAACTTCCCG CCGCCGTTGT TGTTTTGGAG CACGGAAAGA CGATGACGGA AAAGAGATC    1500
GTGGATTACG TCGCCAGTCA AGTAACAACC GCGAAAAAGT TGCGCGGAGG AGTTGTGTTT    1560
GTGGACGAAG TACCGAAAGG TCTTACCGGA AAACTCGACG CAAGAAAAAT CAGAGAGATC    1620
CTCATAAAGG CCAAGAAGGG CGGAAAGTCC AAATTG                              1656
```

(2) INFORMATION FOR SEQ ID NO:9:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Luciola lateralis, Phontinus pyralis (xi) SEQUENCE DESCRIPTION: SEQ ID NO:9:

```
ATGGAAAACA TGGAAAACGA TGAAAATATT GTAGTTGGAC CTAAACCGTT TTACCCTATC      60

GAAGAGGGAT CTGCTGGAAC ACAATTACGC AAATACATGG AGCGATATGC AAAACTTGGC     120

GCAATTGCTT TTACAAATGC AGTTACTGGT GTTGATTATT CTTACGCCGA ATACTTGGAG     180

AAATCATGTT GTCTAGGAAA AGCTTTGCAA AATTATGGTT TGGTTGTTGA TGGCAGAATT     240

GCGTTATGCA GTGAAAACTG TGAAGAATTT TTTATTCCTG TAATAGCCGG ACTGTTTATA     300

GGTGTAGGTG TTGCACCCAC TAATGAGATT TACACTTTAC GTGAACTGGT TCACAGTTTA     360

GGTATCTCTA AACCAACAAT TGTATTTAGT TCTAAAAAAG CTTAGATAA AGTTATAACA      420

GTACAGAAAA CAGTAACTAC TATTAAAACC ATTGTTATAC TAGATAGCAA AGTTGATTAT     480

CGAGGATATC AATGTCTGGA CACCTTTATA AAAGAAACA CTCCACCAGG TTTTCAAGCA      540

TCCAGTTTCA AAACTGTGGA AGTTGACCGT AAAGAACAAG TTGCTCTTAT AATGAACTCT     600

TCGGGTTCTA CCGGTTTGCC AAAAGGCGTA CAACTTACTC ACGAAAATAC AGTCACTAGA     660

TTTTCGCATG CCAGAGATCC TATTTTTGGC AATCAAATCA TTCCGGATAC TGCGATTTTA     720

AGTGTTGTTC CATTCCATCA CGGTTTTGGA ATGTTTACTA CACTCGGATA TTTGATATGT     780

GGATTTCGAG TCGTCTTAAT GTATAGATTT GAAGAAGAGC TGTTTTTACG ATCCCTTCAG     840

GATTACAAAA TTCAAAGTGC GTTGCTAGTA CCAACCCTAT TTTCATTCTT CGCCAAAAGC     900

ACTCTGATTG ACAAATACGA TTTATCTAAT TTACACGAAA TTGCTTCTGG GGGCGCACCT     960

CTTTCGAAAG AAGTCGGGGA AGCGGTTGCA AAACGCTTCC ATCTTCCAGG GATACGACAA    1020

GGATATGGGC TCACTGAGAC TACATCAGCT ATTCTGATTA CACCCGAGGG GGATGATAAA    1080

CCGGGCGCGG TCGGTAAAGT TGTTCCATTT TTTGAAGCGA AGGTTGTGGA TCTGGATACC    1140

GGGAAAACGC TGGGCGTTAA TCAGAGAGGC GAATTATGTG TCAGAGGACC TATGATTATG    1200

TCCGGTTATG TAAACAATCC GGAAGCGACC AACGCCTTGA TTGACAAGGA TGGATGGCTA    1260

CATTCTGGAG ACATAGCTTA CTGGGACGAA GACGAACACT TCTTCATAGT TGACCGCTTG    1320

AAGTCTTTAA TTAAATACAA AGGATATCAG GTGGCCCCCG CTGAATTGGA ATCGATATTG    1380

TTACAACACC CCAACATCTT CGACGCGGGC GTGGCAGGTC TTCCCGACGA TGACGCCGGT    1440

GAACTTCCCG CCGCCGTTGT TGTTTTGGAG CACGGAAAGA CGATGACGGA AAAAGAGATC    1500

GTGGATTACG TCGCCAGTCA AGTAACAACC GCGAAAAAGT TGCGCGGAGG AGTTGTGTTT    1560

GTGGACGAAG TACCGAAAGG TCTTACCGGA AAACTCGACG CAAGAAAAAT CAGAGAGATC    1620

CTCATAAAGG CCAAGAAGGG CGGAAAGTCC AAATTG                              1656
```

(2) INFORMATION FOR SEQ ID NO:10:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Luciola lateralis, Phontinus pyralis (xi) SEQUENCE DESCRIPTION: SEQ ID NO:10:

```
Met Glu Asn Met Glu Asn Asp Glu Asn Ile Val Tyr Gly Pro Glu Pro
 1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Leu Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380
```

```
Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
            435                 440                 445

Tyr Gln Val Ala Pro Ala Glu Leu Glu Ser Ile Leu Leu Gln His Pro
450                 455                 460

Asn Ile Phe Asp Ala Gly Val Ala Gly Leu Pro Asp Asp Asp Ala Gly
465                 470                 475                 480

Glu Leu Pro Ala Ala Val Val Val Leu Glu His Gly Lys Thr Met Thr
            485                 490                 495

Glu Lys Glu Ile Val Asp Tyr Val Ala Ser Gln Val Thr Thr Ala Lys
            500                 505                 510

Lys Leu Arg Gly Gly Val Val Phe Val Asp Glu Val Pro Lys Gly Leu
            515                 520                 525

Thr Gly Lys Leu Asp Ala Arg Lys Ile Arg Glu Ile Leu Ile Lys Ala
530                 535                 540

Lys Lys Gly Gly Lys Ser Lys Leu
545                 550

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

AGAGATCCAA TTTATGGAAA C                                           21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

AGCGTGAGAA AATCTGATCA C                                           21

(2) INFORMATION FOR SEQ ID NO:13:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Luciola lateralis (xi) SEQUENCE DESCRIPTION: SEQ ID NO:13:
```

```
ATGGAAAACA TGGAGAACGA TGAAAATATT GTGTATGGTC CTGAACCATT TTACCCTATT      60

GAAGAGGGAT CTGCTGGAGC ACAATTGCGC AAGTATATGG ATCGATATGC AAAACTTGGA     120

GCAATTGCTT TTACTAACGC ACTTACCGGT GTCGATTATA CGTACGCCGA ATACTTAGAA     180

AAATCATGCT GTCTAGGAGA GGCTTTAAAG AATTATGGTT TGGTTGTTGA TGGAAGAATT     240

GCGTTATGCA GTGAAAACTG TGAAGAATTC TTTATTCCTG TATTAGCCGG TTTATTTATA     300

GGTGTCGGTG TGGCTCCAAC TAATGAGATT TACACTCTAC GTGAATTGGT TCACAGTTTA     360

GGCATCTCTA AGCCAACAAT TGTATTTAGT TCTAAAAAAG GATTAGATAA AGTTATAACT     420

GTACAAAAAA CGGTAACTGC TATTAAAACC ATTGTTATAT TGGACAGCAA AGTGGATTAT     480

AGAGGTTATC AATCCATGGA CAACTTTATT AAAAAAAACA CTCCACAAGG TTTCAAAGGA     540

TCAAGTTTTA AAACTGTAGA AGTTAACCGC AAAGAACAAG TTGCTCTTAT AATGAACTCT     600

TCGGGTTCAA CCGGTTTGCC AAAAGGTGTG CAACTTACTC ATGAAAATTT GGTGATCAGA     660

TTTTCTCACG CTAGAGATCC AATTTATGGA AACCAAGTTT CACCAGGCAC GGCTATTTTA     720

ACTGTAGTAC CATTCCATCA TGGTTTTGGT ATGTTTACTA CTTTAGGCTA TCTAACTTGT     780

GGTTTTCGTA TTGTCATGTT AACGAAATTT GACGAAGAGA CTTTTTTAAA AACACTGCAA     840

GATTACAAAT GTTCAAGCGT TATTCTTGTA CCGACTTTGT TTGCAATTCT TAATAGAAGT     900

GAATTACTCG ATAAATATGA TTTATCAAAT TTAGTTGAAA TTGCATCTGG CGGAGCACCT     960

TTATCTAAAG AAATTGGTGA AGCTGTTGCT AGACGTTTTA ATTTACCGGG TGTTCGTCAA    1020

GGCTATGGTT TAACAGAAAC AACCTCTGCA ATTATTATCA CACCGGAAGG CGATGATAAA    1080

CCAGGTGCTT CTGGCAAAGT TGTGCCATTA TTTAAAGCAA AAGTTATCGA TCTTGATACT    1140

AAAAAAACTT TGGGCCCGAA CAGACGTGGA GAAGTTTGTG TAAAGGGTCC TATGCTTATG    1200

AAAGGTTATG TAGATAATCC AGAAGCAACA AGAGAAATCA TAGATGAAGA AGGTTGGTTG    1260

CACACAGGAG ATATTGGGTA TTACGATGAA GAAAAACATT TCTTTATCGT GGATCGTTTG    1320

AAGTCTTTAA TCAAATACAA AGGATATCAA GTACCACCTG CTGAATTAGA ATCTGTTCTT    1380

TTGCAACATC CAAATATTTT TGATGCCGGC GTTGCTGGCG TTCCAGATCC TATAGCTGGT    1440

GAGCTTCCGG GAGCTGTTGT TGTACTTAAG AAAGGAAAAT CTATGACTGA AAAGAAGTA    1500

ATGGATTACG TTGCTAGTCA AGTTTCAAAT GCAAACGTT TGCGTGGTGG TGTCCGTTTT     1560

GTGGACGAAG TACCTAAAGG TCTCACTGGT AAAATTGACG GTAAAGCAAT TAGAGAAATA    1620

CTGAAGAAAC CAGTTGCTAA GATG                                          1644
```

(2) INFORMATION FOR SEQ ID NO:14:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Glu Asn Met Glu Asn Asp Glu Asn Ile Val Tyr Gly Pro Glu Pro
1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45
```

-continued

```
Thr Gly Val Asp Tyr Thr Tyr Ala Glu Tyr Leu Glu Lys Ser Cys Cys
 50                  55                  60

Leu Gly Glu Ala Leu Lys Asn Tyr Gly Leu Val Val Asp Gly Arg Ile
 65                  70                  75                  80

Ala Leu Cys Ser Glu Asn Cys Glu Glu Phe Ile Pro Val Leu Ala
                 85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
                115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
                180                 185                 190

Gln Val Ala Leu Ile Met Asn Ser Ser Gly Ser Thr Gly Leu Pro Lys
                195                 200                 205

Gly Val Gln Leu Thr His Glu Asn Leu Val Ile Arg Phe Ser His Ala
                210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
                260                 265                 270

Glu Thr Phe Leu Lys Thr Leu Gln Asp Tyr Lys Cys Ser Ser Val Ile
                275                 280                 285

Leu Val Pro Thr Leu Phe Ala Ile Leu Asn Arg Ser Glu Leu Leu Asp
                290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
                355                 360                 365

Pro Leu Phe Lys Ala Lys Val Ile Asp Leu Asp Thr Lys Lys Thr Leu
                370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
                435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Pro Ile Ala Gly
```

```
                               -continued 465                 470                 475                 480

Glu Leu Pro Gly Ala Val Val Val Leu Lys Lys Gly Lys Ser Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545
```